(12) United States Patent
Wang et al.

(10) Patent No.: US 10,249,048 B1
(45) Date of Patent: Apr. 2, 2019

(54) METHOD AND SYSTEM FOR PREDICTING BLOOD FLOW FEATURES BASED ON MEDICAL IMAGES

(71) Applicant: BEIJING CURACLOUD TECHNOLOGY CO., LTD., Beijing (CN)

(72) Inventors: Xin Wang, Seattle, WA (US); Youbing Yin, Kenmore, WA (US); Dan Wu, Bellevue, WA (US); Kunlin Cao, Kenmore, WA (US); Yuwei Li, Bellevue, WA (US)

(73) Assignee: Beijing Curacloud Technology Co., Ltd., Beijing (CN)

( * ) Notice: Subject to any disclaimer, the term of this patent is extended or adjusted under 35 U.S.C. 154(b) by 0 days.

(21) Appl. No.: 16/171,690

(22) Filed: Oct. 26, 2018

Related U.S. Application Data

(60) Provisional application No. 62/586,216, filed on Nov. 15, 2017.

(51) Int. Cl.
| | | |
|---|---|---|
| *G06K 9/00* | (2006.01) | |
| *G06T 7/246* | (2017.01) | |
| *G06T 17/00* | (2006.01) | |
| *A61B 5/00* | (2006.01) | |
| *A61B 5/026* | (2006.01) | |
| *A61B 5/021* | (2006.01) | |
| *A61B 5/02* | (2006.01) | |

(52) U.S. Cl.
CPC .............. *G06T 7/251* (2017.01); *A61B 5/021* (2013.01); *A61B 5/02028* (2013.01); *A61B 5/0261* (2013.01); *A61B 5/7264* (2013.01); *A61B 5/7267* (2013.01); *G06T 17/00* (2013.01); *G06T 2207/20084* (2013.01); *G06T 2207/30104* (2013.01)

(58) Field of Classification Search
None
See application file for complete search history.

*Primary Examiner* — Stephen P Coleman
(74) *Attorney, Agent, or Firm* — Bayes PLLC

(57) ABSTRACT

The present disclosure is directed to a method and system for automatically predicting a blood flow feature based on a medical image. The method may include acquiring, by a processor, image patches and a vessel related feature of a vessel tree. Then, the blood flow feature of the vessel tree may be calculated, by the processor, using a learning network based on both the image patches and the vessel related feature of the vessel tree. The learning network includes a multi-model neural network and a tree structure recurrent neural network connected in series. The method and system of present disclosure can perform a quick and accurate prediction for the blood flow feature, such as FFR, of the vessel tree of a target object (such as certain site of human body or animal body) based on both the medical images and vessel related features of the vessel tree of the target object. The predicted FFR may assist the user in pathological diagnosis or other treatment of the target object.

20 Claims, 5 Drawing Sheets

METHOD AND SYSTEM FOR PREDICTING BLOOD FLOW FEATURES BASED ON MEDICAL IMAGES

CROSS-REFERENCE TO RELATED APPLICATION

This application claims the benefit of priority to U.S. Provisional Application No. 62/586,216, filed on Nov. 15, 2017, the entire content of which are incorporated herein by reference.

TECHNICAL FIELD

The disclosure relates to technical field of artificial intelligence, and more specifically relates to a computer-implemented method for automatically predicting blood flow feature based on a medical image, and system thereof and a computer readable medium.

BACKGROUND

Blood flow dynamic characteristic based on fractional flow reserve (FFR) has been known as a reliable parameter for determining and evaluating the optimal treatment plan of the patients with diseased arteries. Clinical trials show that FFR may be used guide treatments of coronary artery stenosis and other vascular diseases. For example, for cardiovascular diseases, if FFR value is larger than 0.8, drug treatment may be selected. Otherwise, intervention treatment may be adopted. Various blood flow features, including FFR, may provide important reference for the physician during cardiovascular diagnosis.

Invasive quantitative measurement remains the clinical gold standard to assessment of the vascular diseases of the human body. Although attempts to introduce non-invasive methods are made to estimate the blood flow features and diagnose vascular diseases of the human body, it is difficult for these non-invasive methods to be implemented in the clinical environment due to computational complexity, the lengthy time consumption, and inaccurate estimation results.

For example, since a majority of the target objects have complicated vessel paths and vessel tree structures, the existing non-invasive methods can not accurately predict the blood flow features such as FFR. Especially, the vessel tree typically includes a large number of vessel paths due to vessel bifurcations or turning, which further complicates the prediction of blood flow features.

The present disclosure provides an improved system and method for automatically predicting a blood flow feature based on a medical image.

SUMMARY

The present disclosure is directed to a method and system for automatically predicting blood flow feature based on a medical image. The disclosed method makes a global optimization of the vessel tree and predict the blood flow feature of the whole vessel tree based on the distribution of the features on the tree structure of the vessel tree. As an example, the method and system may use a learning model such as a tree structure recurrent neural network (RNN) to calculate the blood flow feature (e.g., FFR, etc.) of the vessel tree accurately and quickly.

According to a first aspect, the present disclosure is directed to a computer-implemented method for automatically predicting a blood flow feature based on a medical image. The method may include acquiring, by a processor, image patches and vessel related features of a vessel tree. Then, the blood flow feature of the vessel tree may be calculated, by the processor, using a learning network based on both the image patches and the vessel related feature of the vessel tree. The learning network includes a multi-model neural network and a tree structure recurrent neural network connected in series.

According to a second aspect, the present disclosure may be directed to a system for automatically predicting blood flow feature based on a medical image. The system may include an acquisition interface configured to acquire medical images and a processor. The processor may be configured to reconstruct a 3D model of the vessel tree based on the medical images. The processor may be additionally configured to acquire image patches and a vessel related feature of a vessel tree. The processor may be further configured to calculate the blood flow feature of the vessel tree using a learning network based on both the image patches and the vessel related feature of the vessel tree. The learning network includes a multi-model neural network and a tree structure recurrent neural network connected in series.

According to a third aspect, the present disclosure may be directed to a non-transitory computer readable medium having instructions stored thereon. The instructions, when executed by a processor, perform a method for automatically predicting a blood flow feature based on a medical image. The method may include acquiring image patches and a vessel related feature of a vessel tree. The method may further include calculating the blood flow feature of the vessel tree using a learning network based on both the image patches and the vessel related feature of the vessel tree. The learning network includes a multi-model neural network and a tree structure recurrent neural network connected in series.

The embodiments of present disclosure can perform a quick and accurate prediction of the blood flow feature of the vessel tree of a target object (such as certain site of human body or animal body), such as FFR, based on both the acquired medical images and the vessel related feature of the vessel tree of the target object. The predicted FFR may assist the user in pathological diagnosis or other treatment of the target object.

It is to be understood that the foregoing general description and the following detailed description are exemplary and explanatory only, and are not restrictive of the invention, as claimed.

BRIEF DESCRIPTION OF THE DRAWINGS

In the drawings, which are not necessarily drawn to scale, like numerals may describe similar components in different views. Like numerals having letter suffixes or different letter suffixes may represent different instances of similar components. The drawings illustrate generally, by way of example, but not by way of limitation, various embodiments, and together with the description and claims, serve to explain the disclosed embodiments. When appropriate, the same reference numbers are used throughout the drawings to refer to the same or like parts. Such embodiments are demonstrative and not intended to be exhaustive or exclusive embodiments of the present method, device, or non-transitory computer readable medium having instructions thereon for implementing the method.

DETAILED DESCRIPTION

Figure 1:
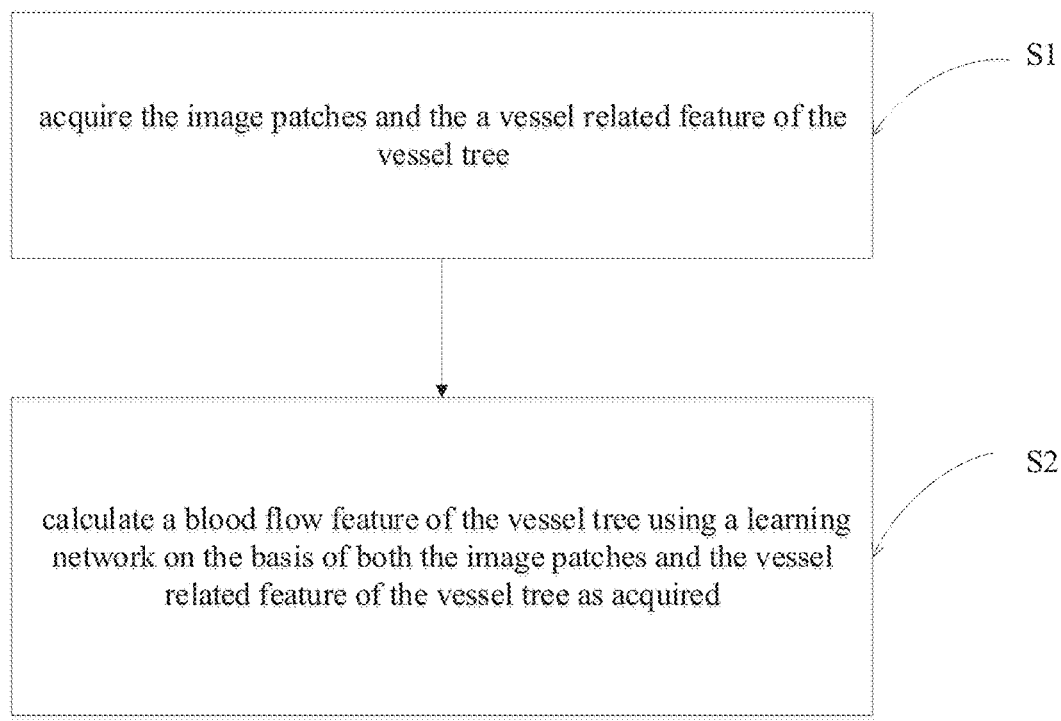
FIG. 1 illustrates exemplary method for predicting blood flow features based on medical images according to some embodiments of present disclosure.

In order to make those skilled in the art to better understand the present disclosure, the embodiments of present disclosure are illustrated in details by referring to the drawings hereinafter. However, the embodiments do not serve as limitations for the present disclosure. The technical term "a feature of the vessel tree" may refer to values of the corresponding feature at a number of measuring points (sampling points) distributed in the vessel tree. That is to say, the technical term "a feature of the vessel tree" may refer to a feature set (a set of the same type of features) of the vessel tree. As an example, the technical term "blood flow of the vessel tree" refers to blood flow values at a number of measuring points distributed in the vessel tree.

In some embodiments, present disclosure may provide a device for automatically predicting a blood flow feature based on medical images. The device may predict the blood flow features of a target object (such as a certain site of the human body or animal body) based on the medical images of the vessels of the target object as acquired (such as by CT). In some embodiments, the blood flow features may include FFR, etc., to assist the user in performing corresponding process on the target object based on the FFR. As an example, the FFR may provide guidance on the treatment of coronary artery stenosis and other vessel diseases. For the cardiovascular diseases, if the FFR is larger than 0.8, then drug treatment may be selected. But if the FFR is less than or equal to 0.8, then intervention treatment may be adopted. The device may include a memory and a processor, which may be communicatively coupled to each other. The processor may be configured to execute the computer executable instructions stored on the memory, e.g. the processor may execute the executable instructions during blood flow feature prediction, to predict the blood flow features based on medical images.

The processor herein may be a processing circuit that includes one or more general processing devices, such as a microprocessor, a central processing unit (CPU), a graphics processing unit (GPU), and the like. More specifically, the processor may be a complex instruction set computing (CISC) microprocessor, a reduced instruction set computing (RISC) microprocessor, a very long instruction word (VLIW) microprocessor, a processor running other instruction sets, or a processor that runs a combination of instruction sets.

The processor may also be one or more dedicated processing devices such as application specific integrated circuits (ASICs), field programmable gate arrays (FPGAs), digital signal processors (DSPs), system-on-chip (SoCs), and the like. As would be appreciated by those skilled in the art, in some embodiments, the processor may be a special-purpose processor, rather than a general-purpose processor. The processor may include one or more known processing devices, such as a microprocessor from the Pentium™ or Xeon™ family manufactured by Intel™, the Turion™ family manufactured by AMD™, or any of various processors manufactured by other providers such as Oracle™ (e.g., SPARC™ architecture processor). The processor may also include graphical processing units (GPU) manufactured by Nvidia™. The disclosed embodiments are not limited to any type of processor(s) otherwise configured to meet the computing demands of identifying, analyzing, maintaining, generating, and/or providing large amounts of imaging data or any other type of data consistent with the disclosed embodiments.

The memory herein may include one or more storage devices configured to store the computer executable instructions to be executed by the processor so as to perform the functions related to the disclosed embodiments. As an example, the memory may store the computer executable instructions for any one of operation system, reconstruction unit, fluid simulation process unit, training unit, and prediction unit. FIG. 1 illustrates the steps to be performed by the prediction unit.

As shown by FIG. 1, the device for predicting the blood flow features based on the medical images may execute computer executable instructions to perform a process including the following steps may be carried out.

The process may begin with Step S1, where the image patches and vessel related feature of the vessel tree may be acquired. A great amount of vessel paths may be included in the vessel tree, and the image patches of the vessel tree may be acquired in various manners. As an example, the image patches of the vessel tree may be obtained by performing image acquisition of the corresponding region of the target object by one or more of various medical imaging apparatuses, e.g., acquiring the images of a cardiac vessel tree of the target object by CT. As another example, the tree structure of the vessel tree may be reconstructed, and the image patches distributed across the vessel tree may be intercepted (cut-out) and obtained at the positions on the centerlines of respective vessels in the tree structure. The image patches may be 2D image patches or 3D image patches. In some embodiments, the vessel related features are also acquired, which may include various related features at the positions of the vessel tree corresponding to the image patches. The vessel related features may include at least one of a first blood flow feature, a vessel structural feature, and a derivative feature.

In some embodiments, the first blood flow feature may be at least one of a fractional flow reserve, a blood flow, a blood flow rate, a micro-vascular resistance, and a blood flow pressure drop. The vessel structural feature may include, but not limited to, the features associated with the 3D or 2D vessel structure (3D image corresponds to 3D vessel structure, and 2D image corresponds to 2D vessel structure), 2D or 1D vessel cross-section structure (3D image corresponds to 2D cross-section structure, 2D image corresponds to 1D cross-section structure), and 1D centerline structure. As an example, 3D (2D) vessel structure associated features may include volume, etc., 2D (1D) vessel cross-section structure associated features may include cross-sectional area, equivalent radius, eccentricity rate, etc., 1D centerline structure associated features may include vessel radius, curvature, length, etc. In addition, the structural feature may include stenosis feature, which reflects the sudden change at the vessel stenosis position compared with adjacent points in the sequence of points on the vessel path and thus can characterize the existence of the stenosis. As an example, the stenosis features may include the area reduction ratios of the vessel sections of the sequence of points on the vessel path, the stenosis position determined according to the area reduction ratios, the stenosis length, etc. Derivative features may be derived according to the vessel structural features. In some embodiments, the derivative features may include the modified features of the vessel structure at the current measuring point, features accumulated along the path from upstream to downstream (or from downstream to upstream) of the vessel, etc. Especially, the features accumulated along the vessel path reflect the influence of the anterior section and/or posterior section of the vessel on the blood vessel features (such as FFR) of the current measuring point of the vessel. In some embodiments, a derivative feature may be obtained based on both the first blood flow feature and the vessel structure feature. As an example, the first blood flow feature and the vessel structure feature may be fused to obtain a compound feature as the derivative feature. As another example, a derivative feature may be obtained based on each of the first blood flow feature and the vessel structure feature and then the two derivative features may be fused to obtain a compound derivative feature.

The first blood flow feature may be obtained by measurements. As an example, the blood flow in the vessel tree may be measured by angiography, and the blood flow rate in the vessel tree may be measured, e.g., by ultrasonic Doppler imaging modality. As another example, the blood flow parameter of the vessel tree may be measured by an invasive catheter. In some embodiments, the first blood flow feature may be calculated by fluid simulation of the vessel tree, at an accuracy lower than that is necessary for diagnosis. As an example, 1D fluid simulation may be performed for the vessel tree to obtain the first blood flow feature. In some embodiments, the fluid simulation may be performed for the vessel tree using coarse initial conditions and boundary conditions. Unlike existing calculation methods that reply on the fluid simulation to calculate the second blood feature such as FFR, etc., step S1 does not rely on the same. Accordingly, the disclosed method improves the calculation speed, reduces the computation resource consumption, lowers the requirement on the operation software platform (e.g., it does not need to purchase and install CFD software), and reduces the operation complexity for the user.

In some embodiments, the image patches and the first blood flow feature may be utilized to predict the second blood flow feature. For example, the image patches along with the blood flow and blood flow rate, etc. may be used as the vessel related features to predict the FFR as the second blood flow feature. In some embodiments, the second blood flow feature may include at least one of a fractional flow reserve, a blood flow, a blood flow rate, a micro-vascular resistance, and a blood flow pressure drop.

The process then proceeds to step S2, where the second blood flow feature of the vessel tree may be calculated by using the learning network based on both the acquired image patches and vessel related features of the vessel tree. The learning network may be an algorithmic model, which imitates the animal neural network action characteristics and performs distributed parallel information processing. The learning network may adjust the mutual connection relationships among a great number of nodes within the system depending on the complex degree of the system. The learning network may have a preliminary adaptive and self-organizational capability, such as changing the weight values of the synapses to satisfy the requirements of the surrounding environments during the learning or training. Therefore, the learning network may be utilized to accurately simulate the related blood flow feature of the respective measuring points in the vessel, and further calculate the second blood flow feature of the vessel tree (such as FFR as intended by the users). Based on the image patches distributed in the vessel tree, the local information and spatial information within the vessel tree may be learned by using the learning network. At the same time, based on the vessel related feature distributed in the vessel tree, the learning network may be utilized to learn about the same. In this manner, various modalities of information of the vessel tree associated with the second blood flow feature to be predicted may be substantially learned, and thus further improving the prediction accuracy and the convergence speed of the calculation. In some embodiments, the learning network may include a multi-model neural network and a tree structure RNN connected with each other in series. Since the tree structure RNN corresponds to morphology of the true vessel tree of the target object, it accounts for the mutual influences among respective branches and among respective positions in the vessel tree. Further, the tree structure RNN makes sufficient use of the compound information (multi-modality and vessel related feature) provided by the tree-shaped structure of the vessel tree as a whole, and thus can achieve efficient global optimization for the vessel tree. By means of the tree structure RNN, the blood flow feature distributed in the whole vessel tree, especially the blood flow feature on the respective vessel path (e.g., including the blood flow feature at the vessel bifurcation which is difficult obtain other neural networks), may be accurately simulated and acquired, to calculate the second blood flow feature of the vessel tree such as FFR, etc.

In some embodiments, the first blood flow feature and the second blood flow feature may not be the same feature, and thus the second blood flow feature may be calculated by using the learning network based on the image patches and the first blood flow feature. In some other embodiments, the first blood flow feature and the second blood flow feature may be the same feature, but the first blood flow feature may not be accurate enough. Therefore, the first blood flow feature may serve as a coarse estimate of the blood flow feature, which can be refined as the second blood flow feature by using the learning network.

Figure 2:
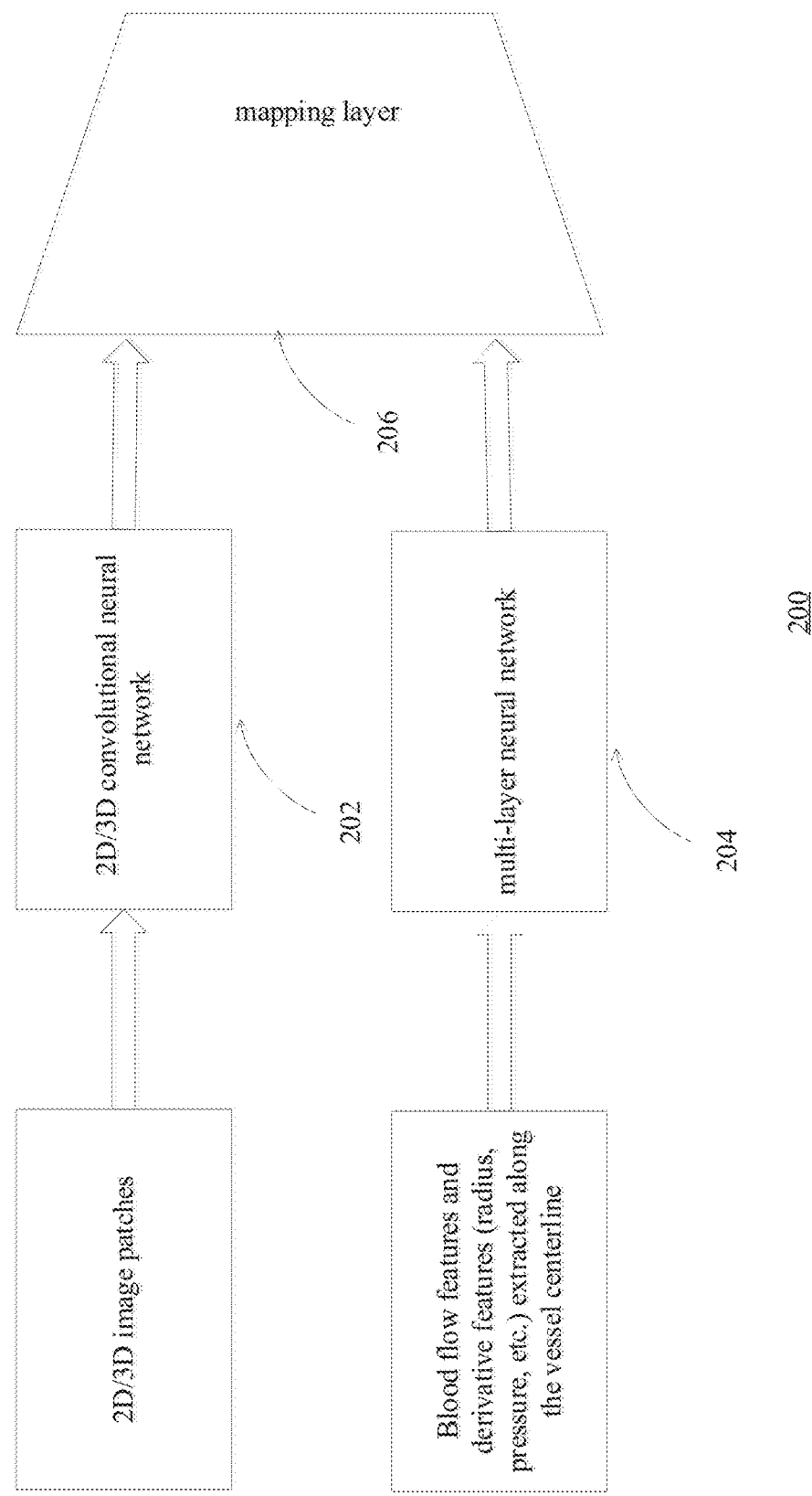
FIG. 2 illustrates an exemplary multi-layer neural network according to some embodiments of present disclosure.
Figure 3:
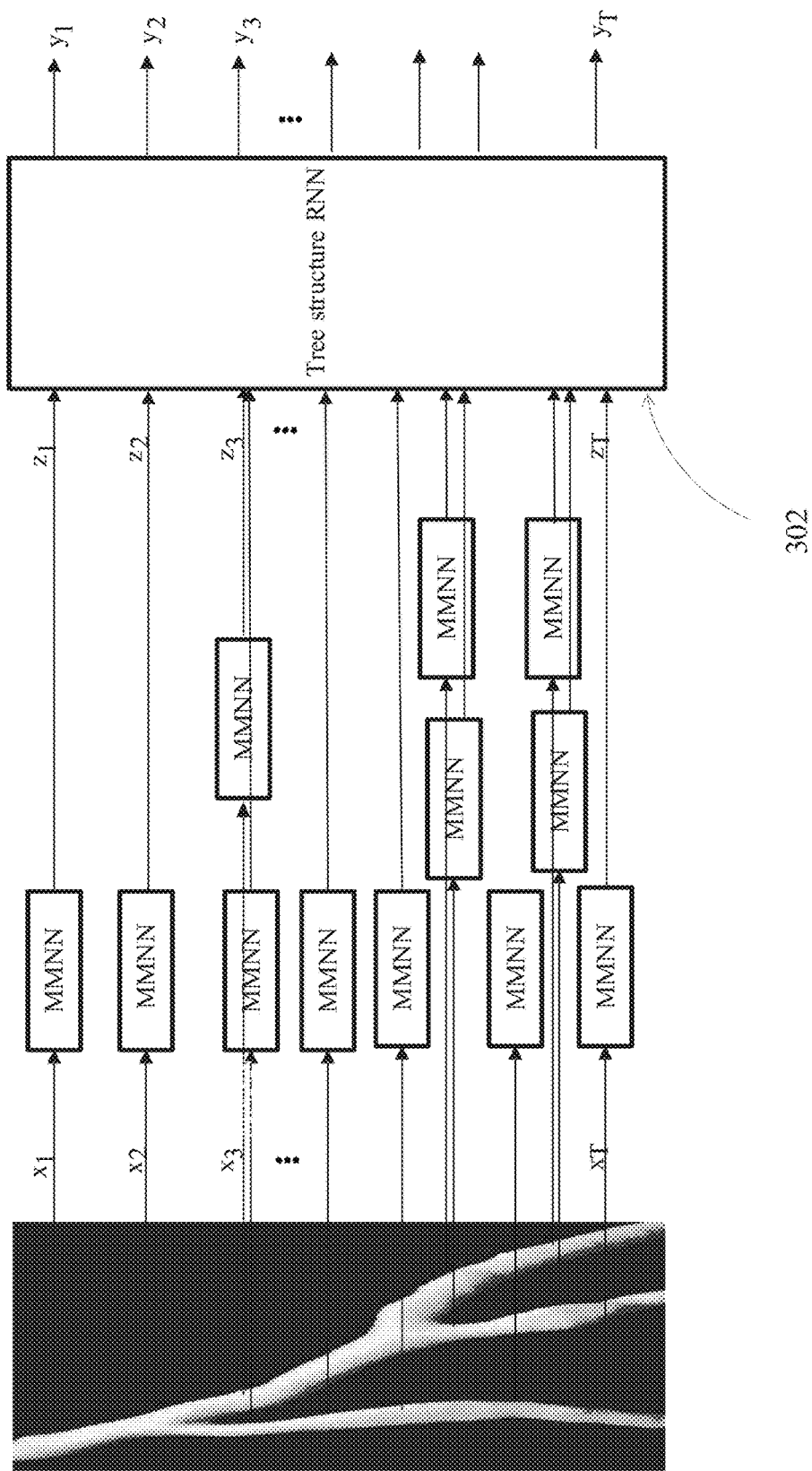
FIG. 3 illustrates a configuration of an exemplary learning network according to some embodiments of present disclosure.

In the embodiment of FIG. 2, a multi-model neural network 200 may include a convolutional neural network 202 and a multi-layer neural network 204. Convolutional neural network 202 may be used to learn the local information and spatial information while multi-layer neural network 204 may be used to learn the above described vessel related features. The output from 2D/3D convolutional neural network 202 and multi-layer neural network 204 may be both mapped to a continuous feature vector through a mapping layer 206. The feature vector may be then transmitted to a tree structure RNN 302 (as shown in FIG. 3). Finally, tree structure RNN 302 outputs the prediction result of the blood flow feature such as FFR, etc. of the whole vessel tree.

By reference to both FIG. 2 and FIG. 3, in some embodiments, based on 2D or 3D image patches distributed in the vessel tree (which may serve as a part of the input $X_i=(x_1, x_2, \ldots, x_T)$), convolutional neural network 202 may learn the local information and spatial information from the image patches, and then the learned information may be sent to mapping layer 206. The first blood flow features extracted along the vessel centerline of the vessel tree and their derivative features (which may serve as another part of the input $X_i=(x_1, x_2, \ldots, x_T)$) may be fed into multi-layer neural network 204 for learning and the learned information is also sent to mapping layer 206. Mapping layer 206 may fuse the learned information from both convolutional neural network 202 and multi-layer neural network 204 and output the same as a continuous feature vector $Z_i=(z_1, z_2, \ldots, z_T)$. $Z_i$ may be transmitted to tree structure RNN 302, which in turn outputs $Y_i=(y_1, y_2, \ldots, y_T)$, the prediction result of the second blood flow feature, e.g. FFR, etc.

In some embodiments, the image patches may be 2D image patches or 3D image patches. The image patches of the vessel tree may be obtained by image acquisition of corresponding region of the target object by various medical imaging apparatuses. As an example, the 2D image patches or 3D image patches may be acquired by CT. The structure and other parameters of the vessel tree (including the vessel paths) may be obtained accurately from the 2D image patches or 3D image patches.

In some embodiments, the above described image patches may be obtained along the respective vessel centerlines of the vessel tree. But the image patches may be intercepted at other positions in other orientations. Particularly, for a vessel tree with a known structure, image patches of a fixed size may be intercepted at a number of measuring points along the centerline. The vessel related features, i.e., the vessel structural features and the derivative features thereof, of the respective measuring points may also be obtained along the centerline.

Figure 4:
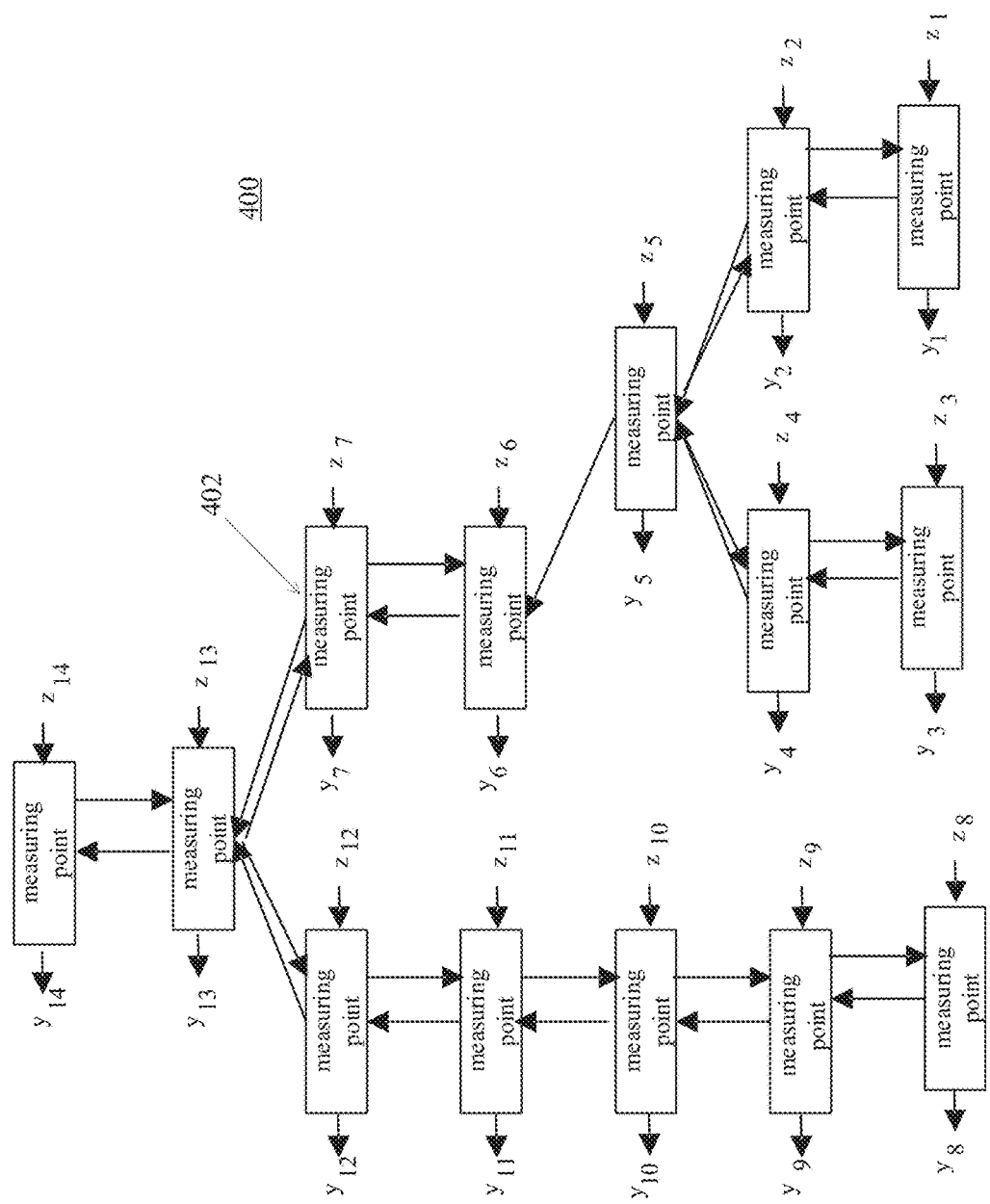
FIG. 4 illustrates a structural schematic diagram of an exemplary tree structure RNN according to some embodiments of present disclosure.

In the embodiment of FIG. 4, the tree-shaped structure of a tree structure RNN 400 may correspond to that of the vessel tree. Accordingly, tree structure RNN 400 may better simulate the tree-shaped structure of the vessel tree and thus predict the vessel related feature of the vessel tree more accurately. In some embodiments, as shown in FIG. 4, the vessel tree may include multiple vessel paths, with a great amount of vessel paths with bifurcation or turning structures. Tree structure RNN 400 is powerful in simulating and calculating blood flow features even with the presence of vessel bifurcations or mutual influences among different vessels. The advantage of the tree-shaped structure of tree structure RNN 400 may become obvious especially for the human organs with a complex vessel tree, such as the heart. Each measuring point 402 may have an input and an output. As shown in FIG. 4, a total of 14 measuring points 402 are included in tree structure RNN 400. As an example, the result $z_i$ (i=1, 2, ..., 14) calculated using multi-layer neural network 204 and convolutional neural network 202 may serve as the input of the individual measuring point 402 of tree structure RNN 400, and the result $y_i$ calculated by tree structure RNN 400 may serve as the output of the corresponding measuring point, so that the second blood flow feature (such as FFR values) of the entire vessel tree may be further calculated. As an example, each measuring unit may adopt a bidirectional RNN, such as a gated recurrent unit (GRU) or a long short-term memory (LSTM) neural network, which is efficient in processing and predicting sequential data.

In some embodiments, the tree structure RNN may include multiple RNNs so as to calculate the second blood flow features of the vessel tree in different directions. Referring back to FIG. 4, in some embodiments, each RNN may calculate the second blood flow features of the vessel tree from upstream to downstream or from downstream to upstream along the corresponding branch of the tree-shaped structure respectively. The multiple RNNs in tree structure RNN 400 may calculate the second blood flow features (such as FFR value) of the vessel tree simultaneously, to improve the operation speed. Further, in some embodiments, in the respective measuring points 402 of the vessel tree, parameters of the parent nodes are updated based on the information of all the child nodes, thus bringing the respective measuring points into close contact with each other. As a result, the calculated second blood flow feature may reflect the integral blood flow feature distribution within the vessel tree.

Exemplary methods described herein can be implemented by a machine such as a computer. The methods may also be implemented as instructions encoded on a computer-readable medium or machine-readable medium, operable to configure an electronic device to perform the methods as described in this disclosure. An implementation of such methods can include software code, such as microcode, assembly language code, a higher-level language code, or the like. Such software code can include computer readable instructions for performing various methods. The software code may form portions of computer program products. Further, in an example, the software code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like. In another embodiment of present disclosure, a computer readable storing medium may be provided with computer executable instructions stored thereon. When the computer executable instructions are executed by the processor, at least some steps of the above methods may be carried out, e.g., acquiring the image patches and the vessel related features of the vessel tree, and calculating the second blood flow feature of the vessel tree by using the learning network based on both the acquired image patches and vessel related features. When the computer executable instructions are executed by the processor, the respective steps or the combination thereof as illustrated in FIG. 2, FIG. 3, and FIG. 4 may be carried out.

Figure 5:
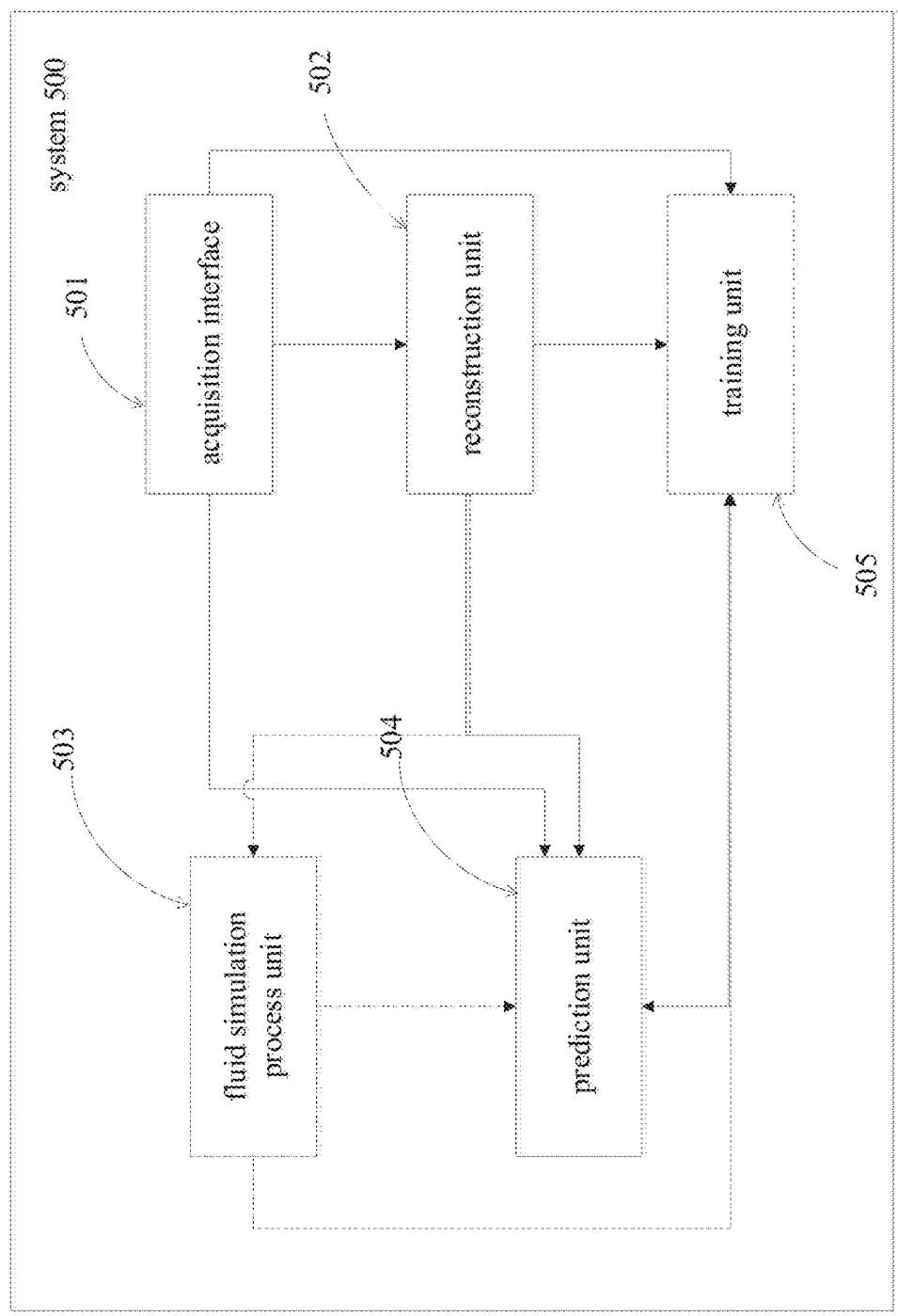
FIG. 5 illustrates a block diagram of an exemplary system for predicting blood flow feature based on medical images according to some embodiments of present disclosure.

The present disclosure also provides a system 500 for predicting blood flow features based on medical images. As shown in FIG. 5, system 500 includes an acquisition interface 501, a reconstruction unit 502, and a prediction unit 504. Acquisition interface 501 may be configured to acquire medical images. Reconstruction unit 502 may be configured to reconstruct a 3D model of the vessel tree based on the medical images acquired by acquisition interface 501. Prediction unit 504 may be configured to perform the above described various methods to predict the second blood flow features based on the reconstructed medical images. These modules (and any corresponding sub-modules or sub-units) can be hardware units (e.g., portions of an integrated circuit) of the processor designed for use with other components or software units implemented by the processor through executing at least part of a program. The program may be stored on a computer-readable medium, and when executed by the processor, it may perform one or more functions.

Acquisition interface 501 may acquire medical images from database (comprising various forms of database, such as local database, cloud database) or image acquisition apparatus (such as CT, MRI, Ultrasound machines, etc.), which may include history medical images or newly acquired medical images, as needed. The reconstruction unit 502 may construct the 3D model of the target object (such a certain organ of the patient) based on the acquired medical images, wherein the 3D model is consistent with the real target object and may reflect the particular structural features of the target object accurately.

The above described prediction unit 504 may be configured to predict second blood flow features (such as FFR, etc.,) of the target object (such as a certain organ of the patient) based on the medical images, based on the information provided by both acquisition interface 501 and reconstruction unit 502. Particularly, prediction unit 504 may be configured to acquire both the image patches and the vessel related features (set) of the vessel tree and calculate the second blood flow features (set) of the vessel tree by using the learning network based on both the acquired image patches and the vessel related features (set) of the vessel tree. Further, the vessel related features may be determined based on the parameters of the 3D model of the vessel tree received from the reconstruction unit. In one example, the vessel related features may be determined based on the parameters of the 3D model of the vessel tree by reconstruction unit 502 and then transmitted to the prediction unit 504. As another example, the determination may be performed by prediction unit 504, or performed in other software modules and transmitted to prediction unit 504.

In some embodiments, system 500 may optionally include a fluid simulation process unit 503, which is configured to perform fluid simulation calculation based on the reconstructed 3D model of the vessel tree to obtain the first blood flow features. The first blood flow features may be of a lower accuracy than that of the second blood flow features. The above described first blood flow features may serve as the boundary conditions of the fluid simulation calculation.

The image patches, based on which prediction unit 504 makes the prediction, may be obtained by using acquisition interface 501. And the vessel related features of the vessel tree, based on which prediction unit 504 makes the prediction, may be obtained by various means. The vessel related features of the vessel tree may be determined by reconstruction unit 502 based on the parameters of the 3D model of the vessel tree received from reconstruction unit 502. Besides, it may be directly determined by measurement or calculated by fluid simulation process unit 503. In some embodiments, fluid simulation process unit 503 may be configured to perform fluid simulation calculation based on the reconstructed model of the vessel tree by adopting coarse initial and boundary conditions and/or reduced model such as 1D model to obtain the first blood flow features. The first blood flow features may be of a lower accuracy than that of the second blood flow features.

In some embodiments, the vessel related features may include at least one of the first blood flow features, the vessel structural features, and the derivative features, and the first blood flow features may include at least one of FFR, blood flow, blood flow rate, micro-vascular resistance, and blood flow pressure drop.

In some embodiments, system 500 may further include a training unit 505 or communicatively coupled to training unit 505. Training unit 505 may be configured to acquire the set of image patches and vessel related feature as well as the corresponding third blood flow feature as training dataset and train the learning network using the training dataset. Particularly, the learning network may be trained by using the training dataset including the image patches, the vessel related features, and the third blood flow features at respective positions of the vessel tree, to obtain the trained learning model, which may be used by the above described device (unit) for predicting the blood flow features of the target object. The third blood flow feature may be obtained by measurement. Besides, the predicted second blood flow feature may be used as the training dataset together with its corresponding image patches and vessel related features. In some embodiments, the predicted second blood flow features together with its corresponding image patches and vessel related features may be stored in the local or remote memory as training dataset, to be accessed and retrieved by training unit 505.

In some embodiments, the learning network may include a multi-model neural network and a tree structure RNN connected with each other in series, wherein the multi-model neural network may include at least one of a convolutional neural network and a multi-layer neural network. During the training process, the parameters of the convolutional neural network, multi-layer neural network, and/or the tree structure RNN may be calculated by means of a stochastic gradient descent method until the corresponding target function converges. The tree structure RNN may be trained by means of the training methods of normal RNN, since the feed-forward network is not connected with the feed-backward network by a side therebetween in the tree structure RNN. Particularly, the integral neural network including the multi-model neural network and the tree structure RNN has a parameter V for the multi-model neural network portion and a parameter W for the tree structure RNN, both of which may be jointly optimized. In some embodiments, the parameter set (V, W) may be optimized by means of a stochastic gradient descent method, and the target function may be defined by the following Equation (1).

$$J(V, W) = \frac{1}{d}\sum_{k=1}^{d} \|y - \hat{y}\|_2 \qquad \text{Equation (1)}$$

The gradient $\nabla_{v,w} J(V, W)$ may be calculated by backward propagation, wherein d refers to the number of the measuring points in the training dataset; y refers to the value of the third blood flow features in the training dataset, and $\hat{y}$ refers to the value of the second blood flow features predicted by the system.

System 500 may include one or more high-performance calculating devices, which may identify, analyze, maintain, generate, or provide a great amount of data, consistent with the disclosed embodiments. System 500 may be separate, or it may be a part of a subsystem and the subsystem serves as a part of an even larger system. As an example, system 500 may include distributed high-performance servers located remotely and communicate with each other through a network such as internet or a dedicated network such as a local area network (LAN) or a wide area network (WAN). In some embodiments, system 500 may include an embedded system, an imaging scanner (such as MR scanner or CT scanner, etc.), and/or a touch control screen display device communicatively coupled to one or more high capability calculating device located remotely.

Moreover, while illustrative embodiments have been described herein, the scope includes any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as non-exclusive. Further, the steps of the disclosed methods can be modified in any manner, including by reordering steps or inserting or deleting steps. It is intended, therefore, that the descriptions be considered as examples only, with a true scope being indicated by the following claims and their full scope of equivalents.

The above description is intended to be illustrative, and not restrictive. For example, the above-described examples (or one or more aspects thereof) may be used in combination with each other. Other embodiments can be used, such as by one of ordinary skill in the art upon reviewing the above description. Also, in the above Detailed Description, various features may be grouped together to streamline the disclosure. This should not be interpreted as intending that an unclaimed disclosed feature is essential to any claim. Rather, inventive subject matter may lie in less than all features of a disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A computer-implemented method for automatically predicting a blood flow feature based on a medical image, comprising:
    acquiring, by a processor, image patches and a vessel related feature of a vessel tree;
    calculating, by the processor, the blood flow feature of the vessel tree using a learning network based on both the image patches and the vessel related feature of the vessel tree, wherein the learning network includes a multi-model neural network and a tree structure recurrent neural network connected in series.

2. The method of claim 1, wherein the blood flow feature includes at least one of a fractional flow reserve, a blood flow, a blood flow rate, a micro-vascular resistance, and a blood flow pressure drop.

3. The method of claim 1, wherein the vessel related feature includes at least one of an initial blood flow feature, a vessel structural feature, and a derivative feature, and each of the initial blood flow feature.

4. The method of claim 1, wherein the vessel related feature of the vessel tree is obtained based on a 3D reconstruction of the medical image, by measurement, or by fluid simulation and calculation based on the medical image.

5. The method of claim 1, wherein the multi-model neural network includes a convolutional neural network and a multi-layer neural network.

6. The method of claim 1, wherein the image patches are 2D image patches or 3D image patches.

7. The method of claim 1, wherein both the image patches and the vessel related feature are obtained along a centerline of the vessel tree.

8. The method of claim 1, wherein, a tree-shaped structure of the tree structure recurrent neural network corresponds to a tree-shaped structure of the vessel tree.

9. The method of claim 1, wherein, the tree structure recurrent neural network comprises multiple recurrent neural networks, each configured to calculate the blood flow feature of the vessel tree in a different direction.

10. A system for automatically predicting a blood flow feature based on a medical image, comprising:
    an acquisition interface configured to acquire medical images; and
    a processor configured to:
        reconstruct a 3D model of the vessel tree based on the medical images; acquire image patches and a vessel related feature of the vessel tree; calculate the blood flow feature of the vessel tree by using a learning network based on both the image patches and the vessel related feature of the vessel tree, wherein the learning network includes a multi-model neural network and a tree structure recurrent neural network connected in series.

11. The system of claim 10, wherein the vessel related feature is obtained based on parameters of the 3D model of the vessel tree received from the reconstruction unit.

12. The system of claim 10, wherein the processor is further configured to perform a fluid simulation calculation based on the reconstructed 3D model of the vessel tree to obtain an initial blood flow feature as the vessel related feature, the initial blood flow feature having a lower accuracy than that of the blood flow feature.

13. The system of claim 10, wherein the processor is further configured to:
    acquire a training dataset including training image patches, training vessel related features of the vessel tree, and corresponding third blood flow features, the third blood flow features of the vessel tree being obtained by measurement;
    train the learning network by using the training dataset.

14. The system of claim 10, wherein the multi-model neural network includes a convolutional neural network and a multi-layer neural network.

15. A non-transitory computer readable medium having instructions stored thereon, wherein the instructions, when executed by a processor, perform a method for automatically predicting a blood flow feature based on a medical image, the method comprising:
    acquiring image patches and a vessel related feature of a vessel tree;
    calculating the blood flow feature of the vessel tree using a learning network based on both the image patches and the vessel related feature of the vessel tree, wherein the learning network includes a multi-model neural network and a tree structure recurrent neural network connected in series.

16. The non-transitory computer readable medium of claim 15, wherein the blood flow feature includes at least one of a fractional flow reserve, a blood flow, a blood flow rate, a micro-vascular resistance, and a blood flow pressure drop.

17. The non-transitory computer readable medium of claim 15, wherein the vessel related feature includes at least one of an initial blood flow feature, a vessel structural feature, and a derivative feature.

18. The non-transitory computer readable medium of claim 15, wherein the vessel related feature of the vessel tree is obtained based on a 3D reconstruction of the medical image, by measurement, or by fluid simulation and calculation based on the medical image.

19. The non-transitory computer readable medium of claim 15, wherein the multi-model neural network includes a convolutional neural network and a multi-layer neural network.

20. The non-transitory computer readable medium of claim 15, wherein a tree-shaped structure of the tree structure recurrent neural network corresponds to a tree-shaped structure of the vessel tree.

* * * * *